United States Patent
Theoharides

(10) Patent No.: US 6,635,625 B2
(45) Date of Patent: *Oct. 21, 2003

(54) PROTEOGLYCAN COMPOSITIONS FOR TREATING PROSTATE AND BLADDER INFLAMMATORY CONDITIONS

(76) Inventor: Theoharis C. Theoharides, 14 Parkman St., Brookline, MA (US) 02446

( * ) Notice: Subject to any disclaimer, the term of this patent is extended or adjusted under 35 U.S.C. 154(b) by 23 days.

This patent is subject to a terminal disclaimer.

(21) Appl. No.: 10/329,386

(22) Filed: Dec. 27, 2002

(65) Prior Publication Data

US 2003/0099732 A1 May 29, 2003

Related U.S. Application Data

(63) Continuation of application No. PCT/US02/00476, filed on Jan. 3, 2002, and a division of application No. PCT/US02/00476, filed on Jan. 3, 2002, which is a continuation of application No. 09/771,669, filed on Jan. 30, 2001.

(51) Int. Cl.$^7$ .................. A01N 43/04; A61K 31/715
(52) U.S. Cl. .............. 514/54; 424/400; 424/78.02; 424/78.03; 424/78.05; 424/45; 424/451; 424/464; 514/2; 514/55; 514/62; 514/825; 514/886; 514/887
(58) Field of Search ................. 424/400, 401, 424/78.02, 78.03, 78.05, 45, 451, 464; 514/2, 54, 55, 62, 825, 886, 887

(56) References Cited

FOREIGN PATENT DOCUMENTS

WO 02/060393 A2 * 8/2002

* cited by examiner

*Primary Examiner*—Thurman K. Page
*Assistant Examiner*—Charesse Evans
(74) *Attorney, Agent, or Firm*—Law Offices of Dr. Melvin Blecher; Melvin Blecher

(57) ABSTRACT

Compositions with synergistic anti-inflammatory effects in inflammatory diseases resulting from activation and consequent degranulation of mast cells and followed by secretion of inflammatory biomolecules from the activated mast cells, composed of a heavily sulfated, non-bovine proteoglycan such as shark cartilage chondroitin sulfate C, and one or more of a hexosamine sulfate such as D-glucosamine sulfate, a flavone such as quercetin, an unrefined olive kernel extract that increases absorption of these compositions in various routes of administration, S-adenosylmethionine, a histamine-1 receptor antagonist, a histamine-3 receptor agonist, an antagonist of the actions of CRH, caffeine, and a polyamine.

1 Claim, No Drawings

PROTEOGLYCAN COMPOSITIONS FOR TREATING PROSTATE AND BLADDER INFLAMMATORY CONDITIONS

This application is a continuation/divisional of PCT/US02/00476, filed Jan. 3, 2002, which is a continuation of co-pending U.S. Ser. No. 09/771,669, filed Jan. 30, 2001.

BACKGROUND OF THE INVENTION

The invention is generally related to the treatment of inflammatory conditions. More specifically, the invention is related to compositions containing inhibitors of mast cell activation and secretion such as a proteoglyean that are designed to be used as dietary supplements or adjuvants to conventional approved medications for the relief of inflammatory conditions.

There have been a number of mostly. anecdotal reports that the proteoglycan chondroitin sulfate, as well as glucosamine sulfate, a product of the intestinal breakdown of proteoglycans, may be helpful in relieving the pain of osteoarthritis: Shute N. Aching for an arthritis cure. *US News and World Report*, Feb. 10, 1997. Cowley G. The arthritis cure? *Newsweek*, Feb. 17, 1997; Foreman J., People, and their pets, tout arthritis remedy. *The Boston Globe*, Apr. 7, 1997; Tye L. Treatment gains scientific attention. *The Boston Globe*, Sep. 25, 2000.

A recent meta-analysis showed potential therapeutic benefit of chondroitin sulfate and/or glucosamine in osteoarthritis [McAlindon et al. *J Am Med Assn*. 283:1469 (2000)], while a double-blind clinical trial with glucosamine showed definite benefits in osteoarthritis with respect to both pain and radiographic joint appearance [Reginster et al., *Lancet* 337:252 (2001)]. However, less than 5% of the chondroitin sulfate in commercially available preparations is absorbed orally, because the size of the molecule and the degree of sulfation impede its absorption from the gastrointestinal tract. Furthermore, such commercial preparations use chondroitin sulfate obtained from cow trachea, with the possible danger of contracting spongiform encephalopathy or "mad cow disease". In fact, the European Union has banned even cosmetics that contain bovine-derived products.

Theoharides et al. *British Journal of Pharmacology* 131:1039 (2000) indicated for the first time how proteoglycans such as chondroitin sulfate may work. The paper reported that chondroitin sulfate and, to a lesser degree, glucosamine sulfate, inhibit activation of mast cells that are known to trigger allergy and asthma. This discovery is the basis for Theoharides, U.S. patent applications Ser. No. 09/056,707, filed Apr. 8, 1998 and Ser. No. 09/773,576, filed Feb. 2, 2001.

Mast cells are also now recognized as important causative intermediary in many painful inflammatory conditions [Galli, *N Eng J Med*. 328:257 (1993); Theoharides, *Int J Tissue Reactions* 18:1 (1996)], such as interstitial cystitis and irritable bowel syndrome [Theoharides, *Ann NY Acad, Sci*. 840:619 (1998)], as well as in migraines and possibly multiple sclerosis [Theoharides, *Persp Biol Med*. 26:672 (1983); Theoharides, Life Sci 46:607 (1996)]. In fact, glucosamine was recently considered to be prophylactic for migraines [Russell, *Med Hypoth* 55:195 (2000)].

Mast cells are increasingly implicated in conditions involving inflamed joints, such as in osteoarthritis and rheumatoid arthritis, through activation of local mast cells by, for example, neuropeptides, such as Substance P. Additional indirect evidence also supports the involvement of mast cells in bone resorption: (a) systemic mastocytosis is invariably associated with osteoporosis; (b) inhibition of mast cell mediator release reversed lytic bone changes; (c) depletion of mast cells inhibited bone resorption in organ culture; (d) human synovial mast cells were shown to secrete in response to allergic and non-immunologic stimuli; (e) human mast cells release the cytokine IL-6 and (f) IL-6 has been definitively linked to bone resorption and osteoporosis.

It was recently shown that chondroitin sulfate's ability to inhibit the activation of mast cells compliments the inhibitory effects on mast cell activation of another class of naturally occurring compounds, the flavonoids [Middleton et al. *Pharm Rev* 52:1 (2000)]. Certain plant flavones (in citrus fruit pulp, seeds, sea weed) are now recognized as anti-allergic, anti-inflammatory, anti-oxidant and cytoprotective with possible anti-cancer properties. Only some flavonoids that belong to the subclass of flavones, e.g., quercetin, inhibit mast cell activation.

Quercetin inhibits secretion from human activated mast cells [Kimata et al. *Allergy* 30:501(2000)], and has also been used effectively for the treatment of chronic prostatitis [Shoskes et al., *Urology* 54:960 (1999)]. However, other flavonoids may have opposite effects. Use of the term "bioflavonoids" or "citrus flavonoids" in certain commercial products, therefore, provides little information, and may include molecules that have detrimental effects; for example, soy contains isoflavones that have estrogen-like activity that worsens inflammatory conditions.

U.S. patent applications Ser. Nos. 09/056,707, filed Apr. 08, 1998, and divisional Ser. No. 09/773,576 claim the oral use of proteoglycans, without and with flavonoids, for the treatment of mast cell activation-induced diseases. Absorption of these compositions from the gastrointestinal tract and synergism with other treatment modalities were not addressed in these applications.

Applicant has described the use of antagonists of the action of Corticotropin Releasing Hormone (also known as Corticotropin Releasing Factor) in inhibiting myocardial mast cell activation in myocardial ischemia (copending U.S. patent application Ser. No. 08/858,136, filed May 18, 1997), in treating stress-induced skin disease (U.S. Pat. No. 6,020, 305) and stress-induced migraine headaches (U.S. Pat. No. 5,855,884), the contents of which are incorporated herein by reference. The synergistic effects of the compositions of the present invention that include antagonists of the actions of Corticotropin Releasing Hormone ("CRH") on mast cells were not recognized at the time of the previous studies. The word "antagonists" in connection with CRH is intended herein to include any molecule that prevents the actions of CRH on target cells, and includes, but is not limited to, anti-CRH neutralizing antibodies or binding proteins, or molecules preventing the release of CRH at local sites (see below for details).

Applicant has also described a method for treating patients with mast cell derived molecules-induced interstitial cystitis with histamine-1 receptor antagonists (U.S. Pat. No. 5,994,357). Treatment of mast cell molecules-induced migraines with histamine-1 receptor antagonists is the subject of Theoharides U.S. Pat. No. 5,855,884. Histamine-3 receptor agonists as pharmaceutical agents in mast cell-involved diseases are described in Theoharides U.S. Pat. No. 5,831,259. The contents of these three patents are incorporated herein by reference. At the time of this invention the synergistic effects of the present compositions with such antagonists had not yet been recognized.

An important need therefore exists for compositions for administration to human patients being treated for mast cell-induced inflammatory diseases by various modalities, that are synergistic in that they have stronger effects than the sum of the effects of the individual components, and also synergistic with conventional clinical treatments of inflammatory conditions. "Synergistic" is also intended to mean: "coordinated or correlated action by two or more structures or drugs" [Stedman's Medical Dictionary, 23rd edition, Williams & Wilkins, Baltimore, 1976]. An important need also exists for formulations that increase the absorption from the gastrointestinal tract, nasal passages and skin surface of the compositions of the invention. Such formulations have been discovered, and are described below.

SUMMARY OF THE INVENTION

The invention comprises compositions for human use containing a sulfated proteoglycan and an unrefined olive kernel (seed) oil, and one or more active ingredients selected from the group consisting of a sulfated hexosamine, a flavonoid compound, S-adenosylmethionine ("SAM"), histamine-1 receptor antagonists, histamine-3 receptor agonists, antagonists of the actions of CRH, caffeine, folic acid, rutin, polyunsaturated fatty acids, and polyamines, together with appropriate excipients and carriers, said compositions having improved absorption from the gastrointestinal tract, skin surface, and nasal and pulmonary surfaces, and anti-inflammatory effects synergistic with each other and synergistic with available conventional clinical treatment modalities.

In one embodiment, the sulfated glucosamine is D-glucosamine sulfate, the proteoglycan is non-bovine chondroitin sulfate, and the flavone is quercetin.

In an other embodiment, compositions may also contain antagonists of the effects of CRH on mast cells or other target cells of the myocardium, gastric mucosa, urinary bladder, skin, meningeal membranes, and blood-brain barrier.

In still another embodiment, the present compositions are used against superficial vasodilator flush syndromes.

DETAILED DESCRIPTION OF THE PREFERRED EMBODIMENTS OF THE INVENTION

It has been discovered that a combination of a sulfated proteoglycan, a sulfated D-hexoseamine and a flavone in a unique, unrefined olive kernel oil, with optional CRH antagonists, histamine-1 receptor antagonists, histamine-3 receptor agonists, polyamines and caffeine has synergistic anti-inflammatory effects when used as a dietary supplement, a topical product or an aerosol for nasal or pulmonary adminstration, without or with a conventional clinical treatment for inflammatory diseases. Such inflammatory diseases result from the activation, degranulation and consequent secretion of inflammatory biochemicals from mast cells, and the resultant inflammatory diseases include the group consisting of: allergic inflammation, arthritis (to include osteoarthritis and rheumatoid arthritis), cancer, fibromyalgia, inflammatory bowel disease, interstitial cystitis, irritable bowel syndrome, migraines, angina, chronic prostatitis, eczema, multiple sclerosis, psoriasis, sun burn, periodontal disease of the gums, superficial vasodilator (flush) syndromes and hormonally-dependent cancers.

In a highly preferred embodiment, the sulfated proteoglycan is non-bovine chondroitin sulfate, preferably from shark cartilage, which blocks mast cell activation, degranulation and consequent secretion of inflammatory biochemicals from the mast cells. Other natural sulfated proteoglycans suitable for practicing this invention include keratan sulfate, dermatan sulfate and hyalurdnic acid sodium salt (sodium hyaluronate). A preferred biological source of the chondroitin sulfate is shark cartilage which is more-highly sulfated than the common commercial chondroitin sulfate isolated from cow trachea; the shark cartilage source also avoids the potential dangers associated with bovine sources.

The highly preferred flavone is quercetin which inhibits secretion of inflammatory molecules from mast cells by affecting moesin, a unique 78 kDa mast cell protein [Theoharides et al. *J Pharm Exp Therap* 294:810 (2000)]. In addition to quercetin, other flavones suitable in carrying out the invention include myricetin, genistein, kaempferol and the quercetin glycoside rutin. A highly preferred source of quercetin and its glycoside is the Saphona plant.

The olive kernel (pit) extract component of the inventive compositions is preferably an unrefined (first pressing, filtered, oleic acid-related acidity <1%, water content <5%) oil produced, for one source, on the island of Crete in Greece. This kernel oil is especially prepared by the maker by a process consisting essentially of: (1) washing the kernel mass that remains after the compression of the oil from the olive flesh with water (Sansa); (2) drying the washed kernels in a stream of hot air at about 80 degrees C. to reduce the humidity to about 1%; (3) extracting the dried kernels with hexane and steam; (4) cooling the hexane extract, microfiltering the extract (5 micron pore size) to remove particulate matter; (5) heating the hexane extract at about 40 degrees C. degrees while percolating helium (to avoid oxidation) through the fluid to evaporate the hexane (final <0.5%), which process reduces the water content to <1% and the acidity (as oleic acid) to <3%; and (6) storing the extract in sealed containers. This olive kernel extract surprisingly has the unique property of increasing absorption of the other components of the anti-inflammatory compositions through the intestinal mucosa and skin, and also adds its own content of important anti-oxidants [Bosku, *World Rev Nutr Diet*, 87:56 (2000)], such as omega fatty acids (e.g., eicosapentanoic acid) and alpha tocopherol. Although not claimed herein, it has been claimed that kernel olive extract has cytoprotective, longevity-producing effects [Trichopoulou et al. *Am J Clin Nutr* 61 :1346S (1995); Trichopoulou et al, *Cancer Epid Biomarker Prevention* 9:869 (2000)]. The polyphenols in such olive oil also have anti-inflammatory effects in, for example, arthritis [Martinez-Dominguez et al., *Inflamm. Res.* 50:102 (2001)]. A preferred source of the unrefined olive kernel extract of the invention is: E.B.E.K., Inc., Commercial, Industrial Enterprises of Crete, 118 Ethnikis Antistasecos, Heraklion, Crete, 71306, Greece.

Supplementation of the compositions described above with the methylation reagent S-adenosylmethionine ("SAM") adds antioxidant, anti-inflammatory and cytoprotective properties, particularly in inflammatory joint diseases. Addition of SAM also accelerates metabolism of homocysteine, which amino acid has been implicated in coronary disease, to cysteine, which is harmless. Folic acid may be added to certain of the present formulations for similar reasons.

Another supplement to the basic compositions of the invention is a histamine-1 receptor antagonist, such as diphenhydramine, hydroxyzine, azelastine, azatadine and cyproheptadine. Other histamine-1 receptor antagonists are described in Table 25-1 in Goodman and Gilman's The Pharmaceuticoal Basis of Therapeutics, 9th ed., New York, 1996. Histamine-3 receptor agonists are described in the Theoharides patents listed above.

Inhibitors of mast cell activation and secretion may be used in the treatment of inflammatory processes such as superficial, vasodilator syndrome, e.g., menopausal-associated flush, monosodium glutamate-associated flush, carcinoid flush and niacin-associated flush.

Sources of CRH antagonists include, in addition to the Theoharides patents listed in the Background section above: Neurocrine Biochem. Inc.'s D-Phe 12 Nle Ala32,21, 38hCRH(12-41)NH2, cat no. 1P-36-41; Pfizer non-peptide CP-154,526-1; Sigma Chem., St. Louis anti-CRH polyclonal antiserum; and Pfizer, N.Y. patents and applications: U.S. Pat. No. 6,211,195, U.S. Pat. No. 5,795,905, PCT/IB95/00573, PCT/IB95/00439, U.S. Ser. No. 08/448,539, U.S. Ser. No. 08/481,413, U.S. Ser. No. 09/735,841, and in Owens et al. *Pharm. Rev.* 43:425 (1991).

The preferred concentration range of the proteoglycan, hexosamine sulfate and flavone components of the oral formulations are 10–3,000 mg per tablet or capsule. The preferred concentration range for SAM is 3–1,000 mg per capsule or tablet. Generally, where present, the amounts of the unrefined kernel oil are at least three times those of the other active ingredients, preferably 900–1200 mg. The number of capsules or tablets to be taken per day is determined by the nature and severity of the medical condition, and is readily determinable by the patient's health provider. Other representative formulations are described in the examples below.

The compositions of the invention may be formulated in any standard means of introducing pharmaceuticals into a patient, e.g., by means of tablets or capsules. The compositions of the invention include ointments and creams for skin conditions, mouth washes and toothpaste for periodontal diseases, and solutions for nasal aerosols. Standard excipients and carriers for the active ingredients of the inventive compositions are described in Remington's Pharmaceutical Sciences, Mack Publishing Co., Easton, Pa. Fragrances and flavorings may also be added.

Although not bound by any particular mechanism of action of the components of the claimed compositions, the inventor contemplates that the proteoglycan inhibits the activation and degranulation of the relevant mast cells, while the flavone inhibits the secretion of inflammatory biomolecules from these mast cells. "Activation" and "degranulation" of mast cells are defined herein as is standard and well known in this art, that is, to mean secretion from the activated mast cell of any type of molecule(s) that alone or in combination triggers inflammatory processes.

EXAMPLES

Example 1

Table 1 compares chondroitin sulfate-containing commercial products to the present compositions.

TABLE 1

Comparison of Chondroitin Sulfate-Containing Products to Present Invention

| Product | Most Available Compositions | Present Invention |
|---|---|---|
| Main ingredient | Mixture of chondroitins | Non-bovine chondroitin sulfate, preferably the C type |
| Source | Cow trachea | Shark cartilage |
| Amount per capsule or tablet | 100–300 | 10–3000 mg |
| Degree of sulfation | Low, if any | High |

TABLE 1-continued

Comparison of Chondroitin Sulfate-Containing Products to Present Invention

| Product | Most Available Compositions | Present Invention |
|---|---|---|
| Absorption from g.i. tract | <5% | >15% |
| Target | Unknown | Mast cells, inflammatory cells |
| Other ingredients | Vitamins, fish oils (some preparations) | Flavones, unrefined kernel olive oil, SAM, histamine-1 receptor antagonists, histamine-3 receptor agonists, CRH antagonists, polyamines, caffeine, folic acid |
| Advantages | None known | Anti-allergic, anti-inflammatory, anti-oxidant, cytoprotective |
| Adverse effects | Risk of mad cow disease, spongiform encephalopathy, stomach upset, allergy to fish products | None known |
| Relevant conditions | Osteoarthritis | Allergic inflammation angina, asthma coronary artery disease, arthritis (osteoarthritis or rheumatoid arthritis), chronic prostatitis, eczema, fibromyalgia, interstitial cystitis, irritable bowel syndrome, inflammatory bowel disease, migraines, multiple sclerosis, psoriasis, periodontal disease, flush syndrome, cancer (including hormonally-dependent forms). |
| Scientific publications | None found | Theoharides et al. Br J Pharm 131:1039 (2000) Middleton et al. Pharm Rev 52:673 (2000) |

In all examples, chondroitin sulfate is to assumed to be of a non-bovine variety.

Example 2

Composition For Protecting Against Inflammatory Diseases

Two capsules to be taken orally 2–3 times daily, at least one hour before meals

| Ingredients, per capsule, | mg: |
|---|---|
| * Chondroitin sulfate | 150–300 |
| * D-Glucosamine sulfate | 150–300 |
| * Quercetin | 150–300 |
| * Unrefined olive kernel extract | 900–1200 |

Example 3

Composition For Protecting Against Arthritis

| Ingredients per capsule, | mg: |
|---|---|
| *D-Glucosamine sulfate | 150–300 |
| *Chondroitin sulfate | 150–300 |
| *Sodium hyaluronate | 100–200 |
| *Quercetin | 150–300 |
| *Unrefined olive kernel extract | 900–1200 |

Example 4

Topical Composition For Protecting Against Arthritis

Skin ointment or cream. Apply three times per day to affected areas.

| Ingredients | % by weight |
|---|---|
| *D-glucosamine sulfate | 5 |
| *Chondroitin sulfate | 5 |
| *Sodium hyaluronate | 5 |
| *Bitter willow bark extract | 5 |
| *Quercetin | 3 |
| *Unrefined olive kernel extract | 15 |

Example 5

Composition For Protecting Against Cardiovascular Disease

| Two capsules to be taken orally 2–3 times per day, in mg: | |
|---|---|
| *Chondroitin sulfate | 50 |
| *Kaempferol | 100 |
| *S-adenosylmethionine | 50 |
| *Niacin | 100 |
| *Unrefined olive kernel extract | 900–1200 |
| *Bitter willow bark extract, 5% by weight | |

Example 6

Composition For Protecting Against Periodontal Disease

| Mouthwash: | |
|---|---|
| *Chondroitin sulfate | 0.4 M |
| *Quercetin | 0.4 M |
| *In a standard mouthwash vehicle | |

Example 7

Toothpaste Composition

| Toothpaste, | mg %: |
|---|---|
| *Chondroitin sulfate | 5 |
| *Quercetin | 3 |
| *Optionally, D-glucosamine sulfate | 5 |
| *In a standard toothpaste vehicle | |

Example 8

Sunscreen Composition

| Ingredients | mg % |
|---|---|
| *Chondroitin sulfate | 5 |
| *D-glucosamine sulfate | 5 |
| *Quercetin | 3 |
| *Sun screen (e.g., $TiO_2$) | 5 |

Example 9

Composition For Protecting Against Migraine Headaches

| Ingredients, | mg: |
|---|---|
| *Chondroitin sulfate | 50 |
| *Quercetin | 100 |
| *Azatadine | 4 |
| *Optionally, a CRH-receptor antagonist | |

Example 10

Composition For Protecting Against Relapsing Multiple Sclerosis

| Ingredients, | mg: |
|---|---|
| *Chondroitin sulfate | 50 |
| *Quercetin | 400 |
| *Hydroxyzine | 50 |
| *Optionally, interferon-beta | |

Example 11

Composition For Protecting Against Cystitis And Prostatitis

| Ingredients, | mg: |
|---|---|
| *D-glucosamine sulfate | 50 |
| *Chondroitin sulfate | 100–300 |
| *Sodium hyaluronate | 200 |

-continued

| Ingredients, | mg: |
|---|---|
| *Quercetin | 100–400 |
| *Unrefined olive kernel extract | 900–1200 |

Example 12

Composition For Protecting Against "Flush"

| Ingredients, per capsule: | |
|---|---|
| *Chondroitin sulfate | 50 mg |
| *Quercetin | 150 mg |
| *Bitter willow bark extract | 5% by weight |
| *Optionally, cyproheptadine or azatadine | 4 mg |

Example 13

Cream Composition For Protecting Against Skin Allergy

| Ingredients: | % by weight |
|---|---|
| *Aloe vera | 5 |
| *Non-bovine chondroitin sulfate | 5 |
| *Myricetin | 5 |
| *Alpha-tocopherol | 5 |
| *Unrefined olive kernel extract | 15 |
| *Optionally, azelastine or hydroxyzine | 5 |

Example 14

Composition For Protecting Against Allergy and Allergic Asthma

| Ingredients, | mg |
|---|---|
| Myricetin | 500 |
| Chondroitin sulfate | 200 |
| Optionally, azelastine or hydroxyzine | |

Example 15

Composition For Protecting Against Hormonally-Dependent Cancers

| Ingredients, | mg |
|---|---|
| Quercetin | 150 |
| Genestein | 50 |
| Optionally, tomoxifen or raloxifen | 10 |

Example 16

Composition For Protecting Against Allergic Conjunctivitis

| Ingredients: | |
|---|---|
| *Quercetin | 0.05% |
| *Chondroitin sulfate | 2.0% |
| *Optionally, azelastine | 0.05% |

I claim:

1. A composition for oral use with synergistic anti-inflammatory properties in prostate and bladder conditions induced by the activation of mast cells, consequent degranulation of said cells and subsequent secretion of inflammatory biomolecules, comprising: shark cartilage chondroitin sulfate 150 mg; Saphona plant quercetin; 50 mg; shellfish chitin D-glucosamine sulfate, 130 mg; rooster crown sodium hyaluronate, 20 mg; Saphora plant rutin (quercetin glycoside), 100 mg; microfiltered unrefined olive kernel (pit) extract (acidity less than 3% and water less than 5%), 49%; suspending agents 40 mg beeswax and 20 mg lecithin; in soft gel (from pig gelatin) capsules.

* * * * *